(12) United States Patent
Tao et al.

(10) Patent No.: US 10,561,484 B2
(45) Date of Patent: Feb. 18, 2020

(54) HERNIA MESH AND ITS PREPARATION METHOD

(71) Applicant: The Hong Kong Research Institute of Textiles and Apparel Limited, Hong Kong (HK)

(72) Inventors: Xiaoming Tao, Hong Kong (HK); Wei Zeng, Hong Kong (HK); Yu Yuan, Hong Kong (HK)

(73) Assignee: The Hong Kong Research Institute of Textiles and Apparel Limited, Hong Kong (HK)

( * ) Notice: Subject to any disclaimer, the term of this patent is extended or adjusted under 35 U.S.C. 154(b) by 245 days.

(21) Appl. No.: 15/682,585

(22) Filed: Aug. 22, 2017

(65) Prior Publication Data

US 2018/0049858 A1    Feb. 22, 2018

(30) Foreign Application Priority Data

Aug. 22, 2016  (CN) .......................... 2016 1 0701034

(51) Int. Cl.
| | |
|---|---|
| *A61F 2/00* | (2006.01) |
| *A61L 31/06* | (2006.01) |
| *A61L 31/14* | (2006.01) |
| *B33Y 80/00* | (2015.01) |
| *B33Y 50/00* | (2015.01) |
| *A61L 27/36* | (2006.01) |

(52) U.S. Cl.
CPC ............ *A61F 2/0063* (2013.01); *A61L 31/06* (2013.01); *A61L 31/148* (2013.01); *A61F 2002/0068* (2013.01); *A61F 2210/0004* (2013.01); *A61F 2220/0016* (2013.01); *A61F 2240/001* (2013.01); *A61L 27/36* (2013.01); *B33Y 50/00* (2014.12); *B33Y 80/00* (2014.12)

(58) Field of Classification Search
CPC ............ A61F 2/0063; A61F 2002/0068; A61F 2002/0072
See application file for complete search history.

(56) References Cited

U.S. PATENT DOCUMENTS

| | | | | |
|---|---|---|---|---|
| 2014/0328963 | A1* | 11/2014 | Mark | ...................... B29C 70/20 425/143 |
| 2015/0147421 | A1* | 5/2015 | Te | .......................... B28B 1/001 425/78 |
| 2017/0165908 | A1* | 6/2017 | Pattinson | ............... B33Y 10/00 |

\* cited by examiner

*Primary Examiner* — Tuan V Nguyen

(57) ABSTRACT

The present application relates to a hernia mesh and its preparation method. A preparation method of hernia mesh comprises selecting and adding a first material particle into a filler tube attached to a 3D printer, and making an external pressure pipe connected; heating the filler tube to a first temperature, and maintaining for a first preset time to remove moisture contained in the first material particle; continuously heating the filler tube to a second temperature, and maintaining for a second preset time to completely melt the first material particle; continuously heating filler tube to a third temperature, and using a designed hernia mesh 3D print file to prepare the hernia mesh by the 3D printer. The hernia mesh prepared has controllable pore size, biocompatibility, tensile strength, and elasticity; the preparation process is convenient and quick, reducing the cost; the patient's foreign body sensation and discomfort can be reduced.

10 Claims, 6 Drawing Sheets

S1, selecting and adding a first material particle into a filler tube attached to a 3D printer, and making an external pressure pipe connected S2, heating the filler tube to a first temperature, and maintaining for a first preset time to remove moisture contained in the first material particle S3, continuously heating the filler tube to a second temperature, and maintaining for a second preset time to completely melt the first material particle S4, continuously heating filler tube to a third temperature, and using a designed hernia mesh 3D print file to prepare the hernia mesh by the 3D printer S1, selecting and adding a first material particle into a filler tube attached to a 3D printer, and making an external pressure pipe connected

S2, heating the filler tube to a first temperature, and maintaining for a first preset time to remove moisture contained in the first material particle

S3, continuously heating the filler tube to a second temperature, and maintaining for a second preset time to completely melt the first material particle

S4, continuously heating filler tube to a third temperature, and using a designed hernia mesh 3D print file to prepare the hernia mesh by the 3D printer

Figure 1

| The tested hernia mesh | Adhesive area | Number of experiments | 180° peel strength test | | | | | Standard deviation |
|---|---|---|---|---|---|---|---|---|
| | | | The maximum value | | Average value | | | |
| | | | Load (N) | strength (N/cm) | Load (N) | strength (N/cm) | | |
| M1 | M1-A1 | M1-A1-E1 | 2.28 | 0.91 | 0.83 | 0.33 | | 0.52 |
| | | M1-A1-E2 | 1.90 | 0.76 | 0.55 | 0.22 | | 0.52 |
| | M1-A2 | M1-A2-E1 | 2.47 | 0.99 | 0.86 | 0.34 | | 0.63 |
| | | M1-A2-E2 | 1.54 | 0.62 | 0.43 | 0.17 | | 0.41 |
| | | M1-A2-E3 | 2.66 | 1.06 | 1.01 | 0.40 | | 0.64 |
| | M1-A3 | M1-A3-E1 | 2.30 | 0.92 | 0.91 | 0.36 | | 0.49 |
| | | M1-A3-E2 | 0.87 | 0.35 | 0.19 | 0.08 | | 0.18 |
| | Average value | | 2.00 | 0.80 | 0.68 | 0.27 | | 0.49 |
| | | The first test of each group | | | | | | |
| M1 | M1-A1 | M1-A1-E1 | 2.28 | 0.91 | 0.83 | 0.33 | | 0.52 |
| | M1-A2 | M1-A2-E1 | 2.47 | 0.99 | 0.86 | 0.34 | | 0.65 |
| | M1-A3 | M1-A3-E1 | 2.30 | 0.92 | 0.91 | 0.36 | | 0.49 |
| | Average value | | 2.35 | 0.94 | 0.87 | 0.35 | | 0.55 |

Figure 2

HERNIA MESH AND ITS PREPARATION METHOD

CROSS REFERENCE TO RELATED APPLICATIONS

The present application claims the benefit of Chinese Patent Application No. 201610701034.2 filed on Aug. 22, 2016. All the above are hereby incorporated by reference.

TECHNICAL FIELD

The present application relates to the field of medical supplies, and more particularly, it relates to a hernia mesh and its preparation method.

BACKGROUND OF THE INVENTION 3D printing is a technology based on a digital model file that uses a powder or granular material to construct objects by layer-by-layer printing. 3D printing is usually done using digital technology material printers, and is often used for manufacturing models in the mold manufacturing, industrial design and other fields.

Hernia repair mesh is mainly used in the repair of abdominal hernia. Abdominal wall hernia refers to the bulging of the organs or tissues within the abdominal cavity from the abdominal wall of the weak or defect area. Abdominal wall hernia includes inguinal hernia, umbilical hernia, hernia, incisional hernia and stoma hernia and so on, and the inguinal hernia is the most common. Because the abdominal wall hernia has a high incidence, so its treatment has now become an important social problem.

The placement of synthetic meshes into the body of a patient has become routine in the field of surgical practice. The most common use for mesh implants is the placement into the abdominal cavity for the repair of ventral and incisional hernias. Intraperitoneal onlay mesh technique is indicated in multiple defect hernias as well as for the treatment of large abdominal wall defects with loss of domain in obese patients. The implants are usually fixed by sutures, tacks or anchors. Complications found with Intraperitoneal onlay mesh technique are seroma formation, impaired functionality of the abdominal wall, chronic pain and adhesion formation. Chronic pain (continuous or intermittent pain) persisting for more than 3 months postoperatively is mainly caused by perforating fixation devices with a reported incidence of 5-15% in open and laparoscopic hernia repair operations. The new trends for hernia repair include mini-invasive techniques, in which the hernia defect is closed by a piece of non-absorbable mesh with minimal tension. The follow-up times thus far are short for such procedures, and it seems that recurrence rates of 1% or below could be expected. Also, the general recovery time has become shorter, and the patients are usually encouraged to begin their normal activities with no restrictions within a week after the operation.

The commercially available meshes used in hernia repair today are typically made of various plastics, which can subdivided in to permanent (non-absorbable) or absorbable mesh. The most commonly used piece of hernia repair mesh polyester, polypropylene mesh and expanded polytetrafluoroethylene mesh. Polypropylene and polyester woven mesh material can help the surrounding tissue ingrowth, to improve the organizational strength and tensile strength. Also due to the large mesh macrophages and leukocytes can access, eliminate network of bacteria, so this type of mesh has a good anti-inflammatory effects, once infected, do not have to remove the mesh; however, these two materials are mesh into the abdominal cavity and internal organs cannot contact you because of a large number of animal experiments and clinical observations found that both mesh with the organization if they can produce severe adhesions in the abdominal cavity, gastrointestinal obstruction or fistula. Expanded polytetrafluoroethylene mesh is a microporous material, easy formation of adhesions in contact with abdominal viscera. But fibroblasts and macrophages cannot enter the pores, so the firm repaired and resistance to infection nor polypropylene and polyester mesh and, in the event of infection must be removed in order to control the meshing material. Further, permanent surgical implants (metals, plastics, silicone, etc.) have been shown to cause side effects in many patients because of corrosion, wearing, migration, chronic inflammation and risk of infection. When the foreign material is placed near sensitive organs, the risks of these side effects can be severe to the patient's well being. In the case of hernia surgery, the plastic mesh will always become situated into close contact with the sensitive intra-abdominal organs.

Bioabsorbable meshes made of polyglycolic acid and its lactide copolymer are also known. Since the 1970's, these bioabsorbable materials have been used in surgery as sutures. No major harm to the tissues has been generally reported from use of polyglycolic acid and its lactide copolymer, and these materials also induce fibrogenesis and scar formation to some extent. Unfortunately, sutures and meshes manufactured of polyglycolic acid or its lactide copolymers (with around 10 mol-% of lactide units) tend to lose their strength within about 1 month after implantation, in which time the hernia site would not have enough time to heal and form scar tissue to resist pressure.

Different mesh concepts for adhesion prevention have been developed including coated meshes, developed for separation of peritoneal defects and used for the individual coating of meshes. Large pores and high flexibility increase mesh integration into the abdominal wall and provide good biomechanical function. Examples for coated meshes are Parietex Composite®, Sepramesh® and Proceed®. The idea of integrating mesh and antiadhesive layer in the implant is to separate implant and viscera until the mesh is covered by neomesothelium (after approximately 10 days) and in the following to reduce the foreign body reaction and adhesion formation triggered by the implant. However, using coated meshes may still trigger adverse reaction due to the use of mechanical fixation means such as sutures, tacks and anchors, which may extend from the implant. It is therefore a goal of the present application to provide improved means to prevent or minimize all causes of unwanted tissue adhesion to the implant or its fixtures.

Clinical and experimental studies have shown that lightweight, large-pore hernia meshes, which have been increasingly implanted in clinical routine, possess better biocompatibility as attested to in numerous experimental and pathological studies. Due to lower inflammatory reaction and scar formation, the dynamics of the abdominal wall is preserved with sufficient stability and shrinkage of the mesh surface is reduced. The ideal surgical repair biological material requirements are: implant material causes physical changes within the organization, without chemical activity, does not cause inflammation and foreign body reaction, non-carcinogenic, non-allergenic and highly sensitized, good biocompatibility, without disturbing the electrolyte balance. Certain properties of each mesh, including tensile strength, elasticity, porosity, and method of fabrication, may greatly influence the tissue reaction to the prosthetic.

Although the use of a hernia mesh has been regarded as a basic means in performing hernia repairs, the decisions about which techniques to use are not well defined, and instead the choice depends on tradition, context, and familiarity with the type of hernia. It is extremely important that surgeons understand the full range of physicomechanical properties of mesh materials, particularly the extent to which these properties affect the body's response to the implanted material.

SUMMERY OF THE INVENTION

In order to solve the above technical problems, the present application provides a hernia mesh and a preparation method thereof, which enables the doctor to completely control the various performance of the hernia mesh and rapidly produce the hernia mesh corresponding to the condition according to the different patient condition. At the same time, the effect of tissue attachment and fixation device on the patient is reduced during the use of hernia mesh.

The technical scheme adopted by the application is: providing a preparation method of hernia mesh, comprising the following steps, S1, selecting and adding a first material particle into a filler tube attached to a 3D printer, and making an external pressure pipe connected;

S2, heating the filler tube to a first temperature, and maintaining for a first preset time to remove moisture contained in the first material particle;

S3, continuously heating the filler tube to a second temperature, and maintaining for a second preset time to completely melt the first material particle;

S4, continuously heating filler tube to a third temperature, and using a designed hernia mesh 3D print file to prepare the hernia mesh by the 3D printer.

The preparation method of hernia mesh according to the present application, further comprising:

S6, selecting a second material particle to be melt at a fourth temperature, and spraying the second material particle onto the hernia mesh prepared by the 3D printer.

The preparation method of hernia mesh according to the present application, before step S6, the method further comprises:

S5, conducting a surface treatment to the hernia mesh prepared by the 3D printer to improve a bonding strength between its interface and other material interfaces.

The preparation method of hernia mesh according to the present application, the first material and the second material are biodegradable materials.

The preparation method of hernia mesh according to the present application, the first material is one or more of copolymers of polylactide and polytrimethylene carbonate, copolymers of Poly-4-hydroxybutyrate, polylactide and copolymers of 3-hydroxybutyrate and 3-hydroxy valerate.

The preparation method of hernia mesh according to the present application, the second material is one or more of copolymers of glycolide and lactide and copolymers of 3-hydroxybutyrate and 3-hydroxy valerate.

The preparation method of hernia mesh according to the present application, the first temperature is 110° C.; the second temperature is 170-255° C.; the third temperature is 175-260° C.; the fourth temperature is 180-200° C.; the first preset time is 30 minutes, and the second preset time is 15 minutes.

The present application further provides a hernia mesh prepared by the method according to the above method, including a hernia mesh body for repairing a hernia site and a plurality of hook bodies for fixing the hernia mesh body; a structure of the hernia mesh body is a grid structure, and the plurality of hook bodies are fixedly connected to grid intersections of the hernia mesh body.

The hernia mesh according to the present application, a material of the hernia mesh is a biodegradable material and the structure of the hernia mesh is a core-shell structure.

The hernia mesh according to the present application, a grid size of the hernia mesh body is 0.1-4.0 mm, and a thickness of the hernia mesh body is 200-800 μm.

Compared with the prior art, the present application has the following advantages:

(1) The hernia mesh prepared by 3D print has controllable pore size, biocompatibility, tensile strength, and elasticity, and the hernia mesh in various shapes and reticular structure can be prepared according to the needs, which is suitable for individuals in different conditions and more conducive for the recovery of the patient.

(2) The combination of 3D printing technology and hernia mesh preparation technology makes the preparation process of the hernia mesh convenient and quick, which can reduce the cost of hernia mesh preparation.

(3) The hernia mesh with lightweight, large-pore prepared by the method of the present application not only reduces its weight in the human body, the patient's foreign body sensation and discomfort, but also reduces the tissue inflammatory response caused after the hernia mesh implanted into the body, and meanwhile it also can promote the growth of the body tissue.

(4) The hernia mesh with core-shell structure prepared by the method of the present application can maintain the strength and stiffness of the hernia mesh at the early stage to ensure its stability in operation; in the wound healing period it can be partially degraded, which can improve the flexibility of the late remaining hernia mesh.

(5) The surface hook structure of the hernia mesh provided by the present application is self-adhesive, which can reduce the difficulty and time of hernia repair surgery and avoid human adverse reactions caused by mechanical fixation after the hernia mesh implanted in the human body, thus further reducing the complications and the postoperative recurrence rate.

(6) The biodegradable materials are selected for the preparation, which makes the degradation time consistent with the recovery time of the patient and reducing the foreign body exclusion and pain on the body of the late patients; after the hernia mesh is absorbed by the body, the residual foreign body is small, and it is easy to form a more flexible scab tissue which fits the abdominal wall structure, and there is no need to remove the hernia mesh from the body after surgery.

BRIEF DESCRIPTION OF THE DRAWINGS

The application will now be further described with reference to the accompanying drawings and the accompanying drawings in which:

FIG. 1 is a flow chart of the steps of the first embodiment of the present application;

FIG. 2 is a performance test result table of the hernia mesh prepared according to the first embodiment of the present application;

EMBODIMENT OF THE INVENTION

Figure 3:
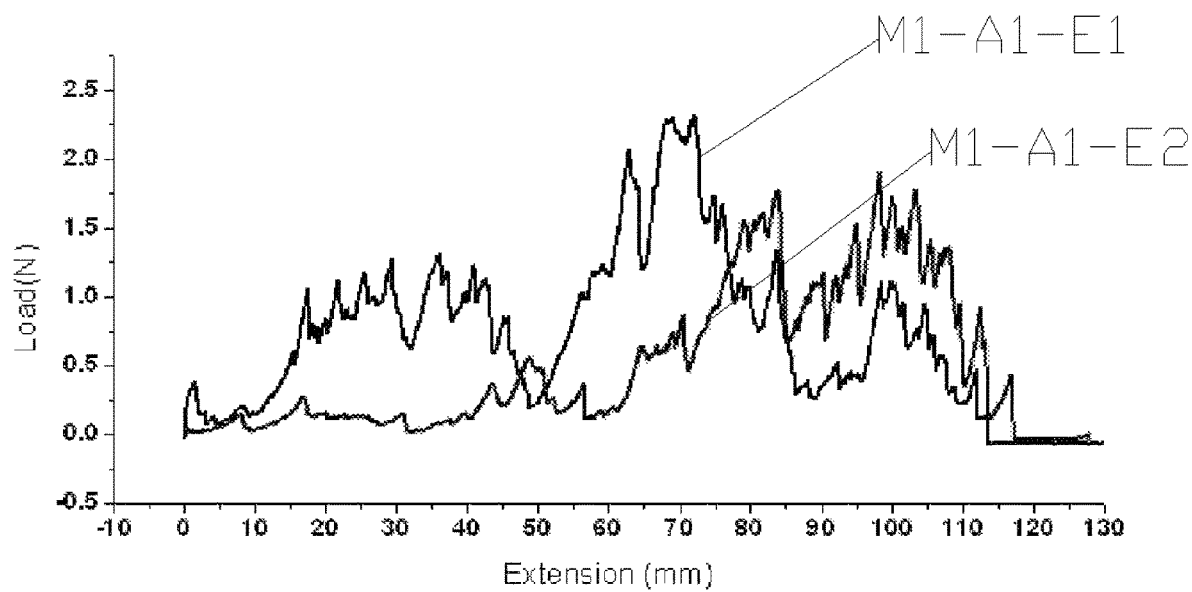
FIG. 3 is a first performance test result chart of the hernia mesh prepared according to the first embodiment of the present application.
Figure 4:
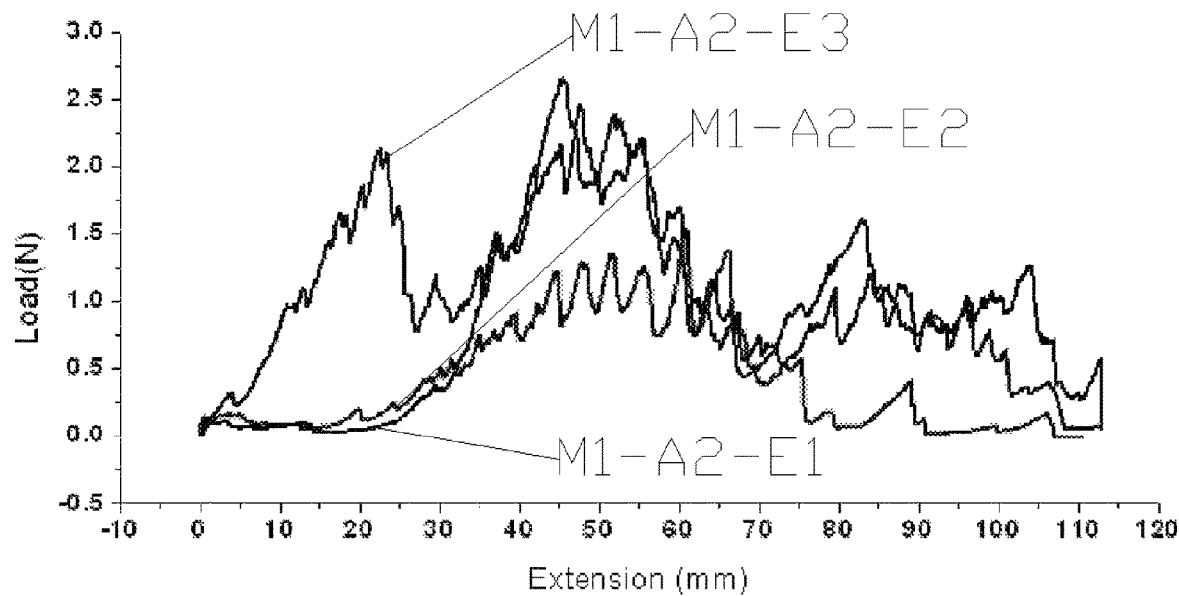
FIG. 4 is a second performance test result chart of the hernia mesh prepared according to the first embodiment of the present application.
Figure 5:
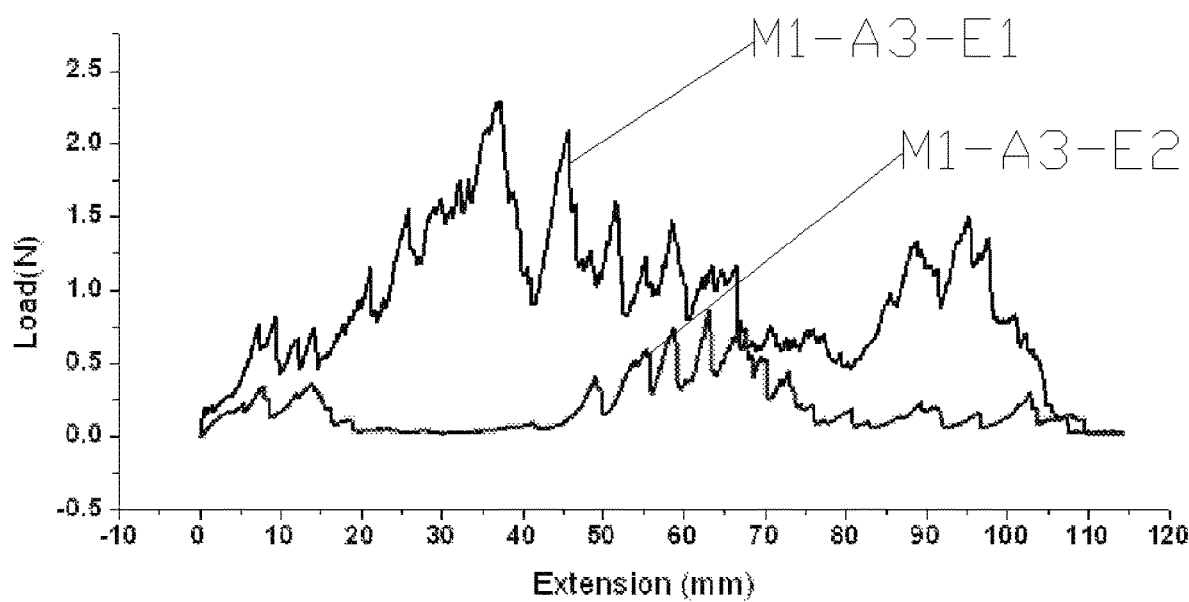
FIG. 5 is a third performance test result chart of the hernia mesh prepared according to the first embodiment of the present application.

To make the objectives, technical solutions and advantages of the present application will become more apparent hereinafter in conjunction with the accompanying drawings and embodiments of the present application will be further described in detail. It is to be understood that the specific embodiments described herein are merely illustrative of the application and are not intended to limit the application.

The First Embodiment

The application provides a convenient and quick method for preparing hernia mesh, which allows the doctor to customize the most suitable hernia mesh in a short time according to the needs of the patient's condition. FIG. 1 is a flow chart of the steps of the first embodiment of the present application; shown in FIG. 1, the first embodiment of the present application comprising the following steps, S1, selecting and adding a first material particle into a filler tube attached to a 3D printer, and making an external pressure pipe connected.

In this step, in order to make the hernia mesh material has good biocompatibility, the first material is biodegradable material. Specifically, it is one or more of copolymers of polylactide and polytrimethylene carbonate, copolymers of Poly-4-hydroxybutyrate, polylactide (PLA) and copolymers of 3-hydroxybutyrate and 3-hydroxy valerate (PHBV). In the present embodiment, the first material is preferably to be a polylactic acid (PLA) material having good biodegradability, thermal stability, bacteriostasis and solvent resistance; the processing temperature is 170~230° C.; it can be processed in a variety of ways, such as extrusion, spinning, biaxial stretching, injection blow molding, and is widely used in the field of health. The 3D printer used in the present embodiment is the 3D-Bioplotter manufactured by ENVISIONTEC, the range of materials used by it to make biological scaffolds is the widest, and it is suitable for the polymer melt, soft gel, hard ceramic and other materials; it is suitable for work in the sterile environment required for biological materials; and it has a good external and internal structure, in line with 3D biological stent requirements required by biological tissue manufacturing, bio-engineering and drug controlled release. The compressed air used in the external pressure pipe is industrial nitrogen with the chemical stability.

S2, heating the filler tube to a first temperature, and maintaining for a first preset time to remove moisture contained in the first material particle.

In this step, in order to make the structure of hernia mesh more compact and complete, before the production the filler tube is heated to a certain temperature to remove moisture contained in the first material particle. In the present embodiment, the first temperature is preferably to be 110° C. and the first preset time is 30 minutes.

S3, continuously heating the filler tube to a second temperature, and maintaining for a second preset time to completely melt the first material particle.

In this step, in order to make the first material into a processable material of the 3D printer, the filler tube is heated to a certain temperature before the production to make the first material particle completely melted. In the present embodiment, the second temperature is preferably to be 170° C. and the first preset time is 15 minutes.

S4, continuously heating filler tube to a third temperature, and using a designed hernia mesh 3D print file to prepare the hernia mesh by the 3D printer.

In this step, in order to make 3D printing more smoothly, the filler tube is continuously heated to the third temperature. In the present embodiment, the third temperature is preferably to be 175° C. The designed hernia mesh 3D print file is designed by the doctor according to the needs of the specific conditions of the patient, and the required hernia mesh is printed and prepared by the 3D printer using the melt deposition method.

The diameter, shape, tensile strength and elasticity and flexibility of the printed hernia mesh can be freely controlled by the procedures of the first embodiment. At the same time the use of biodegradable materials makes it have a good biocompatibility, so that doctors can completely control the performance of hernia mesh, and a hernia mesh corresponding to the disease can be rapidly produced according to different patient conditions.

In connection the hernia mesh prepared by the first embodiment of the present application, the following performance test is made to illustrate the beneficial effects of the present application.

In human anatomy, the hierarchical structure of the anterior abdominal wall (from the surface to the bottom) is: skin, subcutaneous tissue, fascia, muscle layer, abdominal fascia and peritoneum. In hernia repair, the hernia mesh is generally fixed between the abdominal fascia and peritoneum. The pork belly meat having a structure that is similar to the human abdominal wall structure was used as the abdominal wall sample. The selected sample with a length of 19 cm, a width of 11 cm, a height of 1.2~1.5 cm is proceed as follows:

Step 1, maintaining the wetting of the underlying tissue of the sample throughout the course of the test with sterile saline.

Step 2, wrapping the sample tissue with gauze soaked in sterile saline.

Step 3, fixing the sample on the test mold.

Step 4, wiping the surface of the sample with clean gauze.

Step 5, placing a hernia mesh with a length of 15.2 cm and a width of 2.5 cm on the surface of the sample tissue.

Step 6, applying a force of about 5 to 10 N to the area where the hernia mesh is placed so that the hernia mesh is bonded to the sample.

Step 7, clamping the samples on the Instron 5944 tensile testing machine at the appropriate location for testing.

Test Description: Test the maximum tear strength of 1.06N/cm, the minimum 0.35N/cm, is based on GB/T 2790-1995 test method. A specific area of the inner surface of the sample tissue is named M#-A#-E#, where M represents the tested hernia mesh; A represents the bonding area; and E represents the test time. In a group of tensile strength test, including multiple tests, named S#-A#, S represents the number of times, A on behalf of the test area. It should be noted that in multiple tests, the inner surface of the sample will change due to the destruction of the adhesive area caused by the previous test. The average load is calculated based on the overall expansion and standard deviation. The average T-peel strength was calculated by dividing the average load (unit: Newton) by the width of the sample (in cm). Performance test results are shown in FIG. 2, FIG. 3, FIG. 4, and FIG. 5.

As can be seen from the data in the figure, the hernia mesh of the first embodiment of the present application has a better tear resistance and tensile strength. In the practical application, it has a better resistance to abdominal pressure, blocks hernia site, and will not lead to an increased abdominal wall tension, thus reducing the possibility of postoperative pain and recurrence.

The Second Embodiment

In order to improve its biocompatibility and maintain its strength and stiffness in the early stages of hernia mesh, and to maintain a certain amount of support during the wound healing period and finally absorbed by the body, the second embodiment of the present application has developed a hernia mesh with a core-shell structure.

Figure 6:
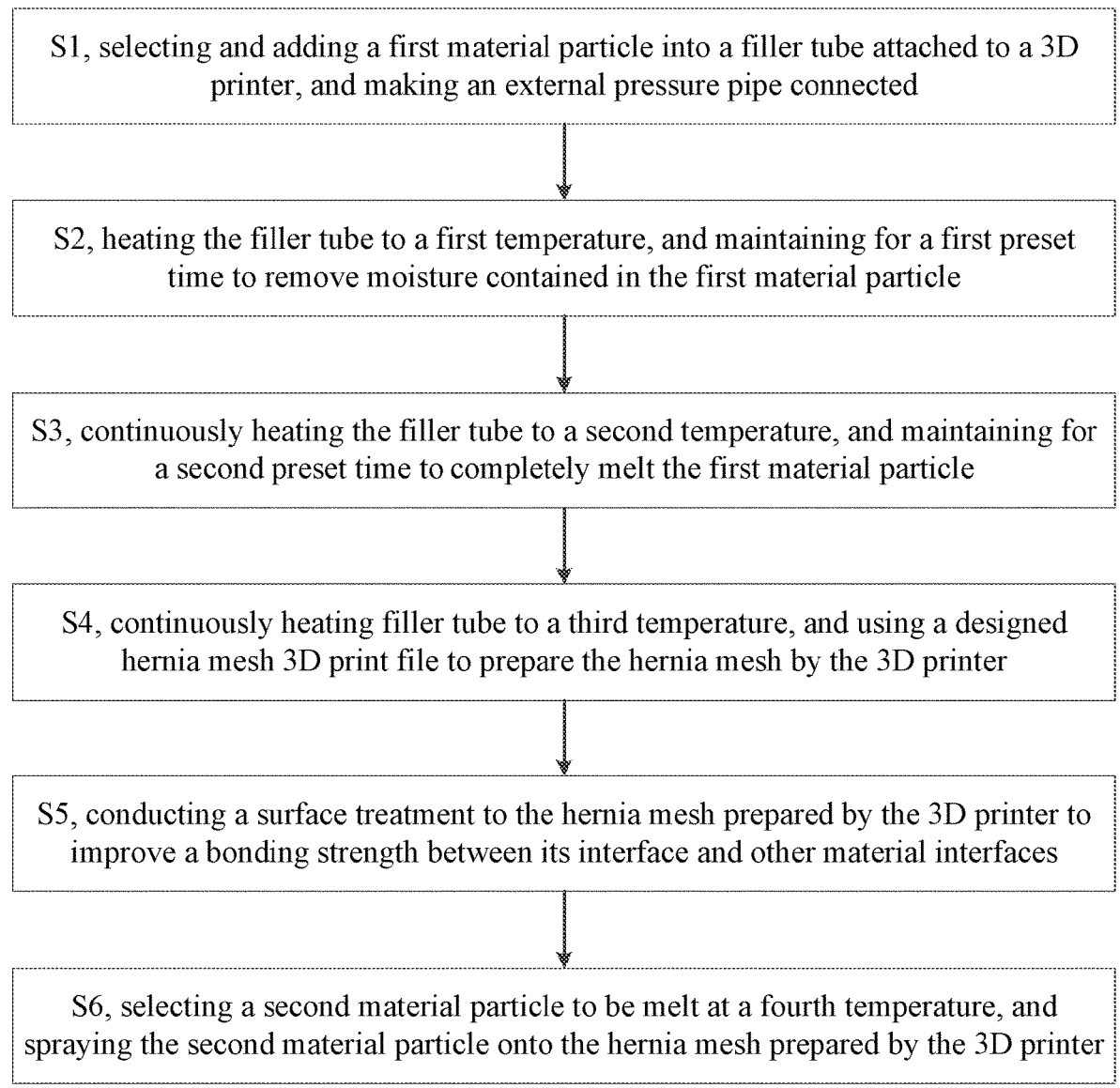
FIG. 6 is a flow chart of the steps of the second embodiment of the present application.

As shown in FIG. 6, the second embodiment of the present application comprising the following steps, S1, selecting and adding a first material particle into a filler tube attached to a 3D printer, and making an external pressure pipe connected.

In this step, in the surgical wound healing period, in order to reduce the stiffness of the hernia mesh to 70% of the initial stiffness and to improve the flexibility and flexibility of the remaining hernia mesh after degradation of the shell material, therefore, the biodegradable polymer with a long degradation time (for 36 months) is selected as the core layer material. In the present embodiment, the first material is preferably to be the copolymer of polylactide and polytrimethylene carbonate. The other is the same as that of the step S1 in the first embodiment.

S2, heating the filler tube to a first temperature, and maintaining for a first preset time to remove moisture contained in the first material particle.

This step is the same as that of step S2 in the first embodiment.

S3, continuously heating the filler tube to a second temperature, and maintaining for a second preset time to completely melt the first material particle.

In this step, the second temperature is 255° C. The other is the same as that of the step S3 in the first embodiment.

S4, continuously heating filler tube to a third temperature, and using a designed hernia mesh 3D print file to prepare the hernia mesh by the 3D printer.

In this step, the third temperature is 260° C., The other is the same as that of the step S4 in the first embodiment.

S5, conducting a surface treatment to the skeleton part of the hernia mesh prepared by the 3D printer to improve a bonding strength between its interface and other material interfaces In this step, preferably, the skeleton part of the hernia mesh is subjected to a plasma surface treatment. By introducing oxygen polar groups on the surface of the skeleton, it can promote the adhesion. Under the same effect, a very thin, high tension coating surface can be obtained by applying plasma treated surface, which is favorable for bonding and coating. So that it does not need other machines, chemical treatment and other strong role in the composition to increase the adhesion S6, selecting a second material particle to be melt at a fourth temperature, and spraying the second material particle onto the skeleton part of the hernia mesh prepared by the 3D printer.

In this step, the second material is the shell material, and can be selected from one or more of copolymers of glycolide and lactide and copolymers of 3-hydroxybutyrate and 3-hydroxy valerate. In the present example, the second material is a copolymer of 3-hydroxybutyrate and 3-hydroxyvalerate (PHBV). Due to the need of the strength and stiffness, its role in the initial stage is very important (sustainable for 2-3 months). The fourth temperature is 180° C.

In the second embodiment, a hernia mesh with core-shell structure is prepared by melting coating method using 3D printer. Shell materials and nuclear layer materials of different ingredient can be selected according to the requirements, which improves the adaptability and pertinence of hernia mesh, greatly improves its biocompatibility, increases its strength and rigidity, and can effectively improve the comprehensive performance of hernia mesh.

The Third Embodiment

Figure 7:
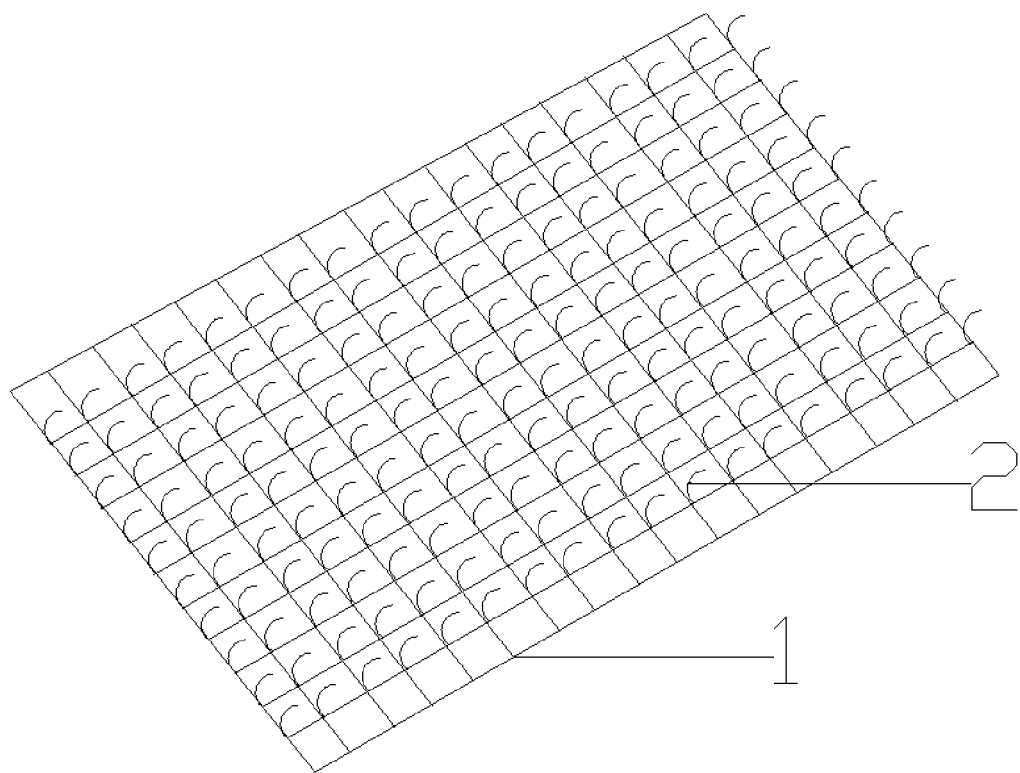
FIG. 7 is a flow chart of the steps of the third embodiment of the present application.

The third embodiment of the application also provides a hernia mesh prepared using the above method. As shown in FIG. 7, the hernia mesh provided by the third embodiment of the application includes a hernia mesh body 1 and a plurality of hook bodies 2 fixedly connected to the grid intersection of the hernia mesh body 1. The hernia mesh body 1 is used for mending the hernia site and blocking the pressure of the abdominal wall to make the hernia site bear more pressure and tensile force. A plurality of hook bodies 2 are used to fix the hernia mesh body 1 at the hernia site. The design can effectively make hernia mesh and the body connected to each other, and prevent the hernia mesh from moving or distorting in the process of human movement while avoiding the use of additional metal or plastic rivets to fix hernia mesh in the body, thus eliminating adverse reactions of the body caused by the mechanical fixation and greatly increasing the patient's comfort. To ensure that the properties of each hernia mesh (such as tensile strength, elasticity, porosity) are controllable, the hernia mesh in the third embodiment of the application is integrally prepared by the 3D printer, and has stronger pertinence and applicability compared with the traditional hernia mesh. In order to improve the biocompatibility of hernia mesh, it is preferable to use biodegradable materials to produce hernia mesh. In order to enhance the comprehensive performance of hernia mesh, the hernia mesh of the third embodiment of the present application is designed as core-shell structure. The shell material is biodegradable materials with shorter degradation times, stiffness and strength, and the nuclear layer material is biodegradable materials with longer degradation time, and flexibility. In this embodiment, the base structure of the hernia mesh is a square grid structure. Due to the advantages of 3D printing, different grid shapes can be chosen, such as triangles, polygons, and circles. At the same time, different grid sizes can also be designed. The hernia mesh pore size preferably used in the present embodiment is 2.0 to 3.0 mm. In this case, it can effectively promote the growth of the body in the grid, and is conducive to the recovery of the wound. At the same time, the thickness of the hernia mesh in this embodiment can be controlled by adjusting the number of layers of the grid structure. The thickness of the hernia mesh is preferably to be 500-600 μm.

Embodiments of the present application have been described above with reference to the accompanying drawings. However, the present application is not limited to the specific embodiments described above, and the above-described embodiments are merely illustrative and not restrictive, It will be apparent to those skilled in the art that various changes may be made therein without departing from the scope of the application as defined by the appended claims and the claims which come within the meaning of the application.

The invention claimed is:

1. A preparation method of hernia mesh, comprising the following steps, S1, selecting and adding a first material particle into a filler tube attached to a 3D printer; S2, heating the filler tube to a first temperature, and maintaining for a first preset time to remove moisture contained in the first material particle; S3, continuously heating the filler tube to a second temperature, and maintaining for a second preset time to completely melt the first material particle; S4, continuously heating filler tube to a third temperature, and using a file designed for 3D printing of the hernia mesh to prepare the hernia mesh by the 3D printer.

2. The preparation method of hernia mesh according to claim 1, further comprising: S6, selecting a second material particle to be melt at a fourth temperature, and spraying the second material particle onto the hernia mesh prepared by the 3D printer.

3. The preparation method of hernia mesh according to claim 2, wherein, before step S6, the method further comprises: S5, conducting a surface treatment to the hernia mesh prepared by the 3D printer to improve a bonding strength between its interface and other material interfaces.

4. The preparation method of hernia mesh according to claim 2, wherein, the first material and the second material are biodegradable materials.

5. The preparation method of hernia mesh according to claim 4, wherein, the first material is one or more of copolymers of polylactide and polytrimethylene carbonate, copolymers of Poly-4-hydroxybutyrate, polylactide(PLA) and copolymers of 3-hydroxybutyrate and 3-hydroxy valerate(PHBV).

6. The preparation method of hernia mesh according to claim 4, wherein, the second material is one or more of copolymers of glycolide and lactide and copolymers of 3-hydroxybutyrate and 3-hydroxy valerate(PHBV).

7. The preparation method of hernia mesh according to claim 5, wherein, the first temperature is 110 degree C.; the second temperature is 170-255 degree C.; the third temperature is 175-260 degree C.; the fourth temperature is 180-200 degree C.; the first preset time is 30 minutes, and the second preset time is 15 minutes.

8. A hernia mesh prepared by the method according to claim 1, comprising a hernia mesh body (1) for repairing a hernia site and a plurality of hook bodies (2) for fixing the hernia mesh body; a structure of the hernia mesh body (1) is a grid structure, and the plurality of hook bodies (2) are fixedly connected to grid intersections of the hernia mesh body (1).

9. The hernia mesh according to claim 8, wherein, a material of the hernia mesh is a biodegradable material and the structure of the hernia mesh is a core-shell structure.

10. The hernia mesh according to claim 8, wherein, a grid size of the hernia mesh body (1) is 0.1-4.0 mm, and a thickness of the hernia mesh body (1) is 200-800 μm.

* * * * *